US007816103B2

(12) United States Patent
Makishima et al.

(10) Patent No.: US 7,816,103 B2
(45) Date of Patent: Oct. 19, 2010

(54) PROTEIN AND PROCESS FOR PREPARING THE SAME

(75) Inventors: Fusao Makishima, Tokyo (JP); Hiroyuki Takamatsu, Saitama (JP); Hideo Miki, Saitama (JP); Shinji Kawai, Saitama (JP); Michio Kimura, Saitama (JP); Tomoaki Matsumoto, Saitama (JP); Mieko Katsuura, Tokyo (JP); Koichi Enomoto, Saitama (JP); Yusuke Satoh, Saitama (JP)

(73) Assignee: Biopharm Gesellschaft zur Biotechnologischen Entwicklung Pharmaka mbH, Heidelberg (DE)

( * ) Notice: Subject to any disclaimer, the term of this patent is extended or adjusted under 35 U.S.C. 154(b) by 384 days.

(21) Appl. No.: 11/833,653

(22) Filed: Aug. 3, 2007

(65) Prior Publication Data

US 2009/0325864 A1 Dec. 31, 2009

Related U.S. Application Data

(62) Division of application No. 10/365,231, filed on Feb. 12, 2003, now Pat. No. 7,268,114, which is a division of application No. 08/945,459, filed as application No. PCT/JP96/01062 on Apr. 19, 1996, now Pat. No. 7,235,527.

(30) Foreign Application Priority Data

Apr. 19, 1995 (JP) ................................. 7/093664
Nov. 17, 1995 (JP) ................................. 7/322403

(51) Int. Cl.
C12P 21/02 (2006.01)
C12N 1/21 (2006.01)
C12N 15/70 (2006.01)
C07K 14/51 (2006.01)

(52) U.S. Cl. ................. 435/69.1; 435/252.3; 435/320.1; 530/350; 536/23.5

(58) Field of Classification Search ....................... None
See application file for complete search history.

(56) References Cited

U.S. PATENT DOCUMENTS

| 4,725,234 A | 2/1988 | Ethridge |
| 5,079,352 A | 1/1992 | Gelfand et al. |
| 5,118,667 A | 6/1992 | Adams et al. |
| 5,143,829 A | 9/1992 | Thompson et al. |
| 5,171,579 A | 12/1992 | Ron et al. |
| 5,354,557 A | 10/1994 | Oppermann et al. |
| 5,658,882 A | 8/1997 | Celeste et al. |
| 5,707,962 A | 1/1998 | Chen et al. |
| 5,994,094 A | 11/1999 | Hotten et al. |

FOREIGN PATENT DOCUMENTS

| EP | 0 433 225 A1 * | 6/1991 |
| EP | 0433225 A1 | 6/1991 |
| EP | 0 625 989 B1 | 1/2000 |
| EP | 0 733 108 B1 | 4/2001 |
| EP | 0 612 348 B1 | 4/2003 |
| WO | 9316099 | 8/1993 |
| WO | WO 93/16099 A2 | 8/1993 |
| WO | 9415949 | 7/1994 |
| WO | 9415949 A1 | 7/1994 |
| WO | WO 95/04819 A1 | 2/1995 |
| WO | WO 95/14778 A2 | 6/1995 |

OTHER PUBLICATIONS

Sherman et al. Methionine or not methionine at the beginning of a protein Bioessays. Jul. 1985;3(1):27-31.*
Munson et al., "lacZ Translation Initiation Mutations", J. Mol. Biol. (1984) 177, pp. 663-683.
Ohkawara et al., "Action Range of BMP is Defined by its N-Terminal Basic Amino Acid Core", Current Biology, vol. 12, p. 205-209, Feb. 5, 2002.
Klein et al., "Protonation States of Methionine Aminopeptidase and Their Relevance for Inhibitor Binding and Catalytic Activity", The Journal of Biological Chemistry, vol. 278, No. 48, Issue of Nov. 28, 2003, pp. 47862-47867.
Yaron et al., "Aminopeptidase-P", J. Biol. Chem., 237, 2207 (1962), pp. 521-535.
Biochemical and Biophysical Research Communications, vol. 204, No. 2 (1994), Hotten et al, "Cloning . . . Factor 5". p. 646-652.
Hsiung et al., "Expression of bovine growth hormone derivatives in Escherichia coli and the use of the derivatives to produce natural sequence growth hormone by cathepsin C cleavage", Methods Enzymol 1987: 153: 390-401.
Ozkaynak et al., "Osteogenic protein-2. A new member of the transforming growth factor-beta superfamily expressed early in embryogenesis", J. Biol. Chem., (Dec. 15, 1992) 267 (35) 25220-7.
Sherman F. et al., "Methionine or not methionine at the beginning of a protein", Bioessays, (Jul. 1985) 3 (1) 27-31.
Ben-Bassat et al., Processing of the initiation methionine from proteins: properties of the Escherichia coli methionine aminopeptidase and its gene structure, J. Bacteriol. Feb. 1987: 169(2): 751-7.
Georgiou G., Optimizing the production of recombinant proteins in microorganisms. AIChE J. (1988), 34 (8), 1233-48.

(Continued)

Primary Examiner—David S Romeo
(74) Attorney, Agent, or Firm—Rothwell, Figg, Ernst & Manbeck, P.C.

(57) ABSTRACT

A protein having amino acid sequence in SEQ ID No.:1 of the Sequence Listing derived from human MP52, and a dimer protein thereof. A homodimer protein described above can be obtained by constructing a plasmid containing DNA coding amino acid sequence in SEQ ID No.:1 of the Sequence Listing with a methionine at the N-terminus, introducing the plasmid into E. coli for transformation, solubilizing inclusion bodies obtained by culturing the transformant, purifying the monomer protein from the solubilized solution, refolding the monomer protein into a dimer protein and purifying the same. The homodimer protein described above is useful as a pharmaceutical composition for treating cartilage and bone diseases.

6 Claims, 7 Drawing Sheets

OTHER PUBLICATIONS

Tonouchi et al, "High-level expression of human BSF-2/IL-6 cDNA in *Escherichia coli* using a new type of expression-preparation System", J. Biochem., (Jul. 1988) 104 (1) 30-34.

Sambrook et al, "Molecular Cloning: A Laboratory Manual Second Edition vols. 1, 2 and 3", Cold Spring Harbor Laboratory Press: Cold Spring Harbor, New York, USA, Nov. 1989, pp. 17-36.

Hirel et al,. "Extent of N-terminal methionine excision from *Escherichia coli* proteins is governed by the side-chain length of the penultimate amino acid", Proc Natl Acad Sci USA, Nov. 1989, 86(21), pp. 8247-8251.

Wang et al, "Recombinant human bone morphogenetic protein induces bone formation", Proc Natl Acad Sci USA, 1990, Mar. 1987 (6), pp. 2220-2224.

Spiro et al., "Inductive activity of recombinant human growth and differentiation factor-5", Biochem Soc Trans. 2000: 28 (4); 362-.

Avis K. E. "Parenteral Preparations", Chapter 84 in Remington's Pharmaceutical Sciences, 18th Edition (Jun. 1990), Mack Pub Co., Easton, Pennsylvania, pp. 1565-1566.

Devlin et al., "Alteration of amino-terminal codons of human granulocyte-colony-stimulating factor increases expression levels and allows efficient processing by methionine aminopeptidase in *Escherichla coli*", Gene, May 15, 1988: 65(1); 13-22.

Luyten F.P., Cartilage-derived morphogenetic protein-1, Int. J. Biochem Cell Biol. Nov. 1997: 29(11):1241-4.

Faiyaz-Ui-Haque et al., Frameshift mutation in the cartilage-derived morphogenetic protein 1 (CDMP1) gene and severe acromesomelic chondrodysplasia resembling Grebe-type chondrodysplasia. Am J Med Genet. Jul. 22, 2002:111(1): 31-7.

Thomas et al., "A human chondrodysplasia due to a mutation in a TGF-beta superfamily member", Nat Genet. Mar. 1996:12 (3): 315-317.

XP-002175388, PREV198886113299 (1 page), 1988.

XP-002106244, (5 pages) "The . . . Receptor Synethesis", 1994.

XP-002175389, (1 page) PREV198579030643 BIOSIS/BIOSIS, 1984.

XP-002058999 (pp. 639-643) "Limb . . . Superfamily", Apr. 14, 1994.

* cited by examiner

SEQUENCE LISTING

```
<160> NUMBER OF SEQ ID NOS: 4

<210> SEQ ID NO 1
<211> LENGTH: 119
<212> TYPE: PRT
<213> ORGANISM: Homo sapiens

<400> SEQUENCE: 1

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
            20                  25                  30

Asp Asp Trp Ile Ile Ala Pro Leu Glu Tyr Glu Ala Phe His Cys Glu
        35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Cys Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115

<210> SEQ ID NO 2
<211> LENGTH: 27
<212> TYPE: DNA
<213> ORGANISM: Artificial sequence
<220> FEATURE:
<223> OTHER INFORMATION: oligonucleotide primer with homolgy to human
      sequence

<400> SEQUENCE: 2
ataatgccac tagcaactcg tcagggc                                           27
```

```
<210> SEQ ID NO 3
<211> LENGTH: 26
<212> TYPE: DNA
<213> ORGANISM: Artificial sequence
<220> FEATURE:
<223> OTHER INFORMATION: oligonucleotide primer with homolgy to human
      sequence

<400> SEQUENCE: 3
cgtcgactac ctgcagccac acgact                                          26

<210> SEQ ID NO 4
<211> LENGTH: 357
<212> TYPE: DNA
<213> ORGANISM: Homo sapiens

<400> SEQUENCE: 4
ccactggcca ctcgccaggg caagcgaccc agcaagaacc ttaaggctcg ctgcagtcgg      60
aaggcactgc atgtcaactt caaggacatg ggctgggacg actggatcat cgcacccctt    120
gagtacgagg ctttccactg cgaggggctg tgcgagttcc cattgcgctc ccacctggag    180
cccacgaatc atgcagtcat ccagaccctg atgaactcca tggaccccga gtccacacca    240
cccacctgct gtgtgcccac gcgactgagt cccatcagca tcctcttcat tgactctgcc    300
aacaacgtgg tgtataagca gtatgaggac atggtcgtgg agtcgtgtgg ctgcagg       357
```

PROTEIN AND PROCESS FOR PREPARING THE SAME

BACKGROUND OF THE INVENTION

1. Field of the Invention

This invention relates to a protein having amino acid sequence in SEQ ID No.:1 of the Sequence Listing derived from MP52. The invention also relates to a homodimer protein of said protein and a pharmaceutical composition for treating cartilage and bone diseases containing the dimer protein as an active ingredient. The invention also relates to a process for preparing the above described protein in a large amount and with a high purity by culturing E. coli which was transformed with a plasmid containing a DNA sequence capable of expressing the above described protein. The invention further relates to a method for treating cartilage and bone diseases, which comprises administering to a human a pharmaceutical composition containing, as an active ingredient, an effective amount of the homodimer protein.

2. Description of the Prior Art

Pharmaceutical compositions comprising vitamin $D_3$, calcitonin, estrogen or their derivatives as well as bisphosphonate derivatives have been used in clinical practice for preventing and treating bone diseases. Recently, bone morphogenetic protein (BMP hereinafter), the TGF-β gene superfamily comprising BMP-2 through BMP-9 and related proteins, have been reported to have bone morphogenetic activity.

Furthermore, the bone morphogenetic activity of one of those proteins called MP52 has been also reported (WO 93/16099 and WO 95/04819). A mature region of MP52 protein is considered to be a protein consisting of 120 amino acid residues having the N-terminal alanine, and its amino acid sequence is described in these publications.

A protein called GDF-5, having an analogous amino acid sequence with MP52, is also described in Nature, vol. 368, p. 639-643 (1994) and WO 94/15949.

However, these proteins can not be easily prepared in a purified form on an industrial scale.

Mammalian cell lines such as L-cells have been tried on for producing MP52 with genetic engineering technology. However, t has been found not easy to prepare MP52 in a purified form and in a high yield with the expression systems.

DETAILED DESCRIPTION OR THE INVENTION

The present inventors have tried to prepare MP52 using E. coli on a large scale by genetic engineering technology. Briefly, the inventors have tried to prepare MP52 using E. coli by adding a codon encoding methionine to the DNA encoding mature region of MP52 which starts from alanine. The resultant product was not MP52 only but a mixture of MP52, a protein of 121 amino acid residues having the N-terminal methionine and a protein of 119 amino acid residues having the N-terminal alanine detached and starting from proline. It was extremely difficult to isolate pure MP52 at least with the mature region from the mixture.

The inventors have found that a protein in SEQ ID No.:1 of the Sequence Listing starting from proline at the N-terminus can be selectively produced in an extremely high yield by constructing a plasmid wherein a codon encoding methionine was connected to the DNA sequence encoding amino acid sequence in SEQ ID No.:1 of the Sequence Listing consisting of 119 amino acid residues with elimination of the N-terminal alanine of MP52, and by using the obtained plasmid-introduced E. coli for expression. Moreover, the homodimer of the protein described in SEQ ID No.:1 in the Sequence Listing was conformed to have a cartilage and bone morphogenetic activity, and thus the invention was completed.

An object of the invention is to provide a protein having amino acid sequence shown in SEQ ID No.:1 of the Sequence Listing. The protein consists of 119 amino acid residues, and corresponds to one in which the N-terminal alanine is eliminated from human MP52 which is regarded as a mature region consisting of 120 amino acid residues. The protein according to the invention is soluble in water. Moreover, the protein is low toxic itself because it is derived from human.

Another object of the invention is to provide a pharmaceutical composition for treating cartilage and/or bone diseases, which comprises as an active ingredient a homodimer of the protein having the amino acid sequence shown in SEQ ID No.:1 of the Sequence Listing. More in detail, the invention relates to a pharmaceutical composition for preventing and treating osteoporosis, osteoarthritis such as gonarthritis deformans and malum coxae deformans, or arthrosteitis, cartilagineous lesion such as articular meniscus lesion, reconstruction in the defective parts of bone and cartilage caused by injury and oncoectomy, defect of bone and cartilage, bone fracture, congenital cartilage and bone diseases such as chondrodysplasia, chondrohypoplasia, achondrogenesis, palatoschisis and osteodysplasia, and furthermore radicular and arvecular defects, since the homodimer protein according to the invention has a cartilage and bone morphogenetic activity. Furthermore, the homodimer protein can be applied to a treatment of bone grafting in cosmetic surgery. These treatments also include those in the area of veterinary surgery.

A further object of the invention is to provide a process for preparing a protein consisting of 119 amino acid residues derived from human MP52 shown in SEQ ID No.:1 of the Sequence Listing using E. coli.

In particular, the invention relates to the construction of a plasmid containing a DNA sequence encoding the amino acid sequence consisting of 119 amino acid residues shown in SEQ ID No.:1 of the Sequence Listing with an additional methionine at the N-terminus. Only the mature region of human MP52 cDNA was amplified by polymerase chain reaction (PCR method) by using, as a template DNA, a plasmid vector containing cDNA described in WO 93/16099. The PCR method referred to herein generally means to multiply a very small amount of fragments of DNA or RNA by the method described in U.S. Pat. No. 4,683,195.

It is necessary for preparing the protein of the invention to construct appropriate expression vectors containing DNA encoding the protein, which are then introduced into desirable E. coli host strains by genetic engineering technology. The following two improved processes were applied for a large scale production of the protein;

1) A process for increasing the productivity of target proteins by increasing the translation efficiency as reported by M. Nobuhara et al. {Agric. Biol. Chem., 52 (6), 1331-1338, 1988}, viz. the method of increasing the AT content around the ATG initiation codon, and 2) A process for increasing an average copy number of plasmids per cell, viz. the method of replacing ori region for the replication origin or pBR vector by that of pUC vector. Further, the expression vector (pKOT245) of the invention was constructed by direct ligation of the promoter region with the DNA sequence encoding amino acid sequence in SEQ ID No.:1 of the Sequence Listing with an additional methionine in its N-terminus. The E. coli containing said vector was deposited (Accession No. BIKOKEN-KI P-14895) at National Institute of Bioscience and Human-Technology, Agency of Industrial Science and Technology which is located at 1-3, Higashi 1-chome, Yatake-cho, Tsukuba-shi, Ibaraki-ken, 305 Japan on Apr. 14, 1995 and transferred to a deposit (Accession No. BIKOKEN-KI BP-5499) on Apr. 10, 1996 according to Budapest Treaty on the International Recognition of the Deposit of Microorganisms.

This invention relates to a process for preparing monomer proteins comprising the steps of:

constructing a plasmid containing DNA encoding amino acid sequence in SEQ ID No.:1 of the Sequence Listing with a methionine at its N-terminus, introducing the plasmid into *E. coli* for transformation, cultivating the *E. coli* to obtain inclusion bodies, solubilizing and purifying said inclusion bodies to obtain monomer proteins, and to a process for preparing homodimer proteins of the protein in SEQ ID No.:1 of the Sequence Listing by refolding and purifying the monomer proteins obtained in the above. Briefly, the proteins of the invention were prepared by solubilizing the *E. coli* inclusion bodies followed by loading on SP-Sepharose FF column and Sephacryl S-200 column to obtain purified sulfonated MP52 monomers, which were subjected to refolding and isoelectric precipitation, then to RESOURCE RPC column of reverse-phase HPLC to obtain the purified dimer fractions of the proteins. The physicochemical properties of the proteins were analyzed on the basis of N-terminal amino acid sequence and amino acid composition and by electrophoresis.

This invention further relates to a process for culturing *E. coli* which were introduced with the expression vectors of the invention under the conditions of culture medium at 28-34° C., pH 6-8 and a dissolved oxygen concentration of 20-50%.

This invention further relates to a method for treating cartilage and bone diseases, which comprises administering to a human a pharmaceutical composition containing, as an active ingredient, an effective amount of the homodimer protein.

Biological activities of the homodimer protein were determined by analysis of soft X-ray radiographs, analysis of tissue-staining and analysis of time-course of ectopic cartilage/bone formation. Furthermore, from the results of the effect on the intramembranous ossification, the effect on the regeneration of articular cartilage and the effect on the healing of bone fracture and defects, the homodimer protein of the present invention is proved to be beneficial to the therapies of cartilage and/or bone regeneration.

The homodimer protein of the invention can be administered in systemic by intravenous, intramuscular or intra-peritoneal injection. In case of intravenous administration, an intravenous drip infusion can also be used, in addition to conventional intravenous injections.

Injectable preparations can be formulated, for example, in the form of injectable powders. In that case, the powders can be prepared by adding one or more of suitable water-soluble excipients such as mannitol, sucrose, lactose, maltose, glucose, fructose and the like, to an active ingredient, dissolving the mixture in water, dividing it into vials or ampoules followed by lyophilizing and hermetically sealing.

In the case of local administration, the homodimer protein can be coated on the surface of cartilage, bone or tooth to be treated with collagen paste, fibrin glue or other adhering materials. In the case of bone grafting, both natural bone and conventional artificial bone can be used. Artificial bone means the bone made of metal, ceramics, glass, and other natural or artificial inorganic substance. Hydroxyapatite is cited as preferable artificial substance. For example, artificial bone can be constructed by steel as dense material in the inner part and hydroxyapatite as porous material in outer part.

Moreover, it is beneficial to apply the homodimer protein to the part from which cancerous bone tissue is removed in order to accelerate the reconstruction of bone. It can also be applied to the cartilage grafting.

The dose may be varied depending upon various factors influencing the activity of the protein such as weight of bone and cartilage to be reconstructed, injured site of bone and cartilage and the symptoms, age and sex of patients, severity of infection, administration intervals and other clinical factors. The dose can also be varied depending upon types of carriers to be used for restructuring with the dimer protein. In general, the dose is in the range of about $10-10^6$ ng of the homodimer protein per wet weight of desired bone and cartilage when administered as a composition containing a carrier. In the case of local and systemic administration by injection, it is preferable to administer $0.1-10^4$ μg in a frequency of from once a week to once a day.

A synergetic effect can be expected by administering the homodimer protein simultaneously with known growth factors, for example, insulin-like growth factor-I for regeneration of bone and cartilage.

There has never been reported of a process for preparing the protein of the invention on an industrial scale and in a purified form as described above, and the homodimer protein is useful as a medical composition for treating cartilage and bone diseases since it has a cartilage and bone morphogenetic activity. Further, the process of preparing the protein of the present invention can be applicable for the preparation of other proteins of the above-described TGF-β superfamily members, all of which were only successful so far to prepare by using mammalian cell lines.

This invention is further illustrated by the following examples. However, it should not be construed that the invention is limited to these specific examples.

EXAMPLE

Example 1

Construction of Expression Vector (1) Isolation of a Mature Region of MP52

A mature region of human MP52 cDNA was PCR-amplified using the plasmid vector (pSK52s) containing cDNA described in WO 93/16099 as a template DNA.

In accordance with the process for increasing a productivity of the target proteins reported by M. Nobuhara, et al. {Agric. Biol. Chem., 52 (6), 1331-1338, 1988}, a part of DNA of the mature region of MP52 gene was substituted to increase the AT content around the ATG initiation codon.

The mutagenesis was introduced by PCR method using the designed upstream PCR primer encompassing the mutation of SEQ ID No.:2 of the Sequence Listing. For the DNA sequence of the PCR primers were used the DNA in the SEQ ID No.:2 as an upstream primer, and the DNA in SEQ ID No.:3 of the Sequence Listing as a downstream primer.

The PCR was performed by adding the template DNA (10 ng), 50 pmols each of the PCR primers in an order direction and in a reverse direction, dNTP (0.2 mmol) and $MgCl_2$ (1.5 mmol) in the same test tube, together with Taq DNA polymerase (5 U).

Thirty cycles of PCR were performed; the conditions of each cycle were 94° C. for a minute for denaturation, 55° C. for a minute for primer annealing, and 72° C. for 2 minutes for primer extension.

The products obtained from the PCR was isolated by electrophoresis in 1.5% low melting point agarose (purchased from FMC), and the fragments of about 360 bp were isolated (Fragment 1).

Figure 1:
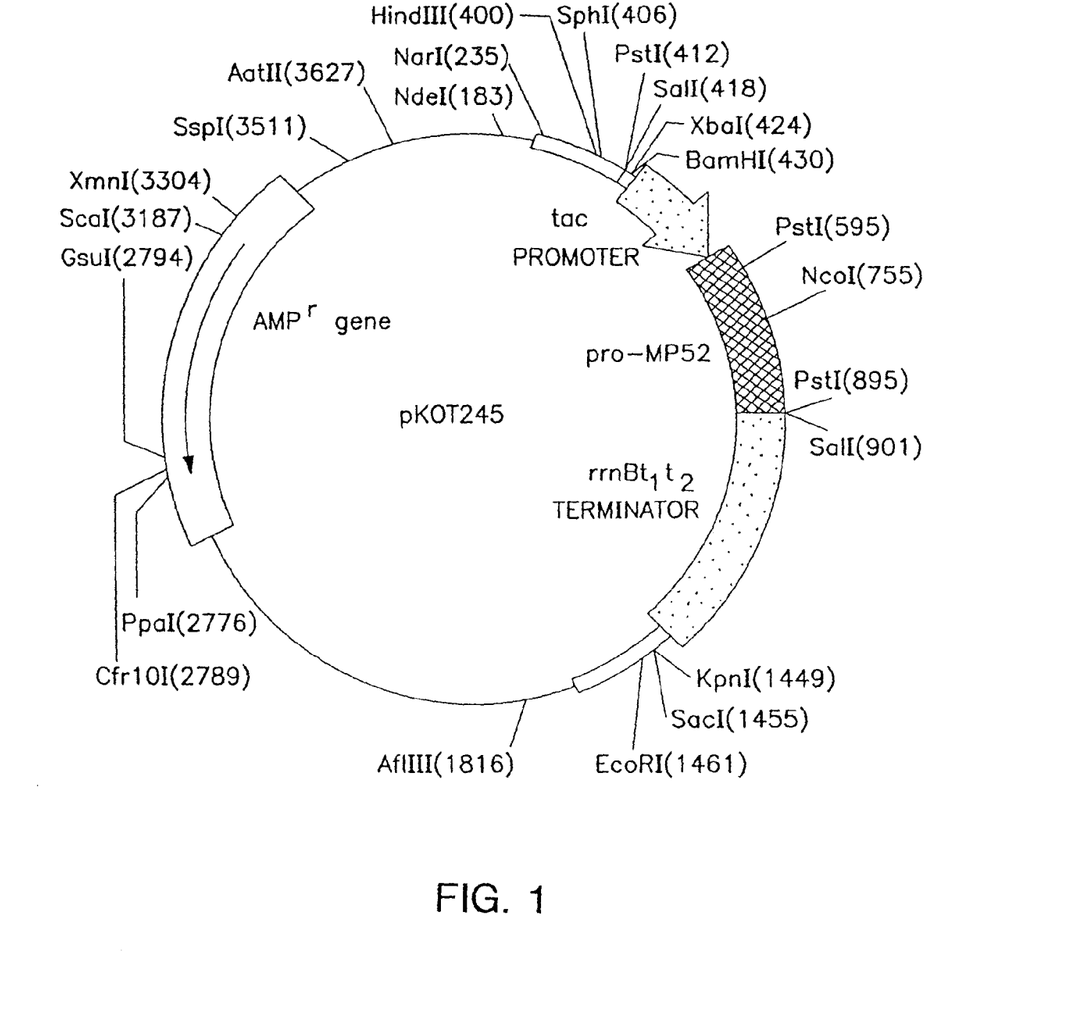
FIG. 1 shows a plasmid map of the expression vector (pKOT245) for the protein of the invention obtained in Example 1 step (2).

(2) Construction of *E. coli* Expression Vector for the Protein of the Invention In order to increase a copy number of the plasmid per bacteria, the ori region for replication origin was changed from that of pBR to pUC vector. The *E. coli* expression vector pKK223-3 available in the market (purchased from Pharmacia Biotech) was used to isolate tac promoter region by digestion with restriction endonucleases SspI and EcoRI, and also to isolate rrnBt$_1$t$_2$ terminator region by using SalI and SspI. A DNA fragment of tac promoter region which had been treated with Mung Bean Nuclease (Takara Shuzo Co., Ltd.) was ligated by T4 DNA ligase with Fragment 1 which was obtained above. The resultant DNA fragment was digested by SalI and re-ligated with the rrnBt$_1$t$_2$ region. The DNA fragment was ligated into the SmaI site of pUC18 vector to construct the expression vector {pKOT245 (Accession No. BIKOKEN-KI P-14895)} (FIG. 1) for the production of the protein. The length of pKOT245 DNA is 3.7 kb. The nucleotide sequence of the expression vector constructed for the protein was analyzed by Pharmacia ALF DNA sequencer.

(3) Transformation

Transformation was performed according to the rubidium chloride transformation method by Kushner et al. (Genetic Engineering, p. 17, Elsevier, 1978). Briefly, pKOT245 was used to transform the host strain *E. coli* W3110M according to the method described above to produce *E. coli* transformants for the production of the protein.

Example 2

Cultivation (1) Cultivation

The *E. coli* expressing the protein of the invention was precultured in the modified SOC medium (Bacto tryptone 20 g/l, Bacto yeast extract 5 g/l, NaCl 0.5 g/l, MgCl$_2$.6H$_2$O 2.03 g/l, Glucose 3.6 g/l). 100 ml of the bacteria suspension was used to inoculate 5 l of the production medium (Bacto tryptone 5 g/l, Citric acid 4.3 g/l, K$_2$HPO$_4$ 4.675 g/l, KH$_2$PO$_4$ 1.275 g/l, NaCl 0.865 g/l, FeSO$_4$.7H$_2$O 100 mg/l, CuSO$_4$.5H$_2$O 1 mg/l, MnSO$_4$.nH$_2$O 0.5 mg/l, CaCl$_2$.2H$_2$O 2 mg/l, Na$_2$B$_4$O$_7$.10H$_2$O 0.225 mg/l, (NH$_4$)$_6$Mo$_7$O$_{24}$.4H$_2$O 0.1 mg/l, ZnSO$_4$.7H$_2$O 2.25 mg/l, CoCl$_2$.6H$_2$O 6 mg/l, MgSO$_4$.7H$_2$O 2.2 g/l, Thiamine HCl 5.0 mg/l, Glucose 3 g/l), which was cultured in a 10-liter fermentor with aeration-agitation, and then upon reaching the early stage of logarithmic growth phase (OD$_{550}$=5.0), isopropyl-β-D-thio-galactopyranoside at a final concentration of 1 mM was added and the cultivation was continued until reaching OD$_{550}$=150. During the cultivation, temperature was kept at 32° C., and pH value of 7.15 by adding ammonia. In order to prevent lowering of a dissolved oxygen concentration, an agitation was sped up to keep the dissolved oxygen concentration at 50% of air saturation. The cultivation was proceeded by adding 50% glucose solution at a level of 0.2% to obtain a high cell density, with an indication of abrupt increase of the dissolved oxygen concentration.

(2) Preparation of *E. coli* Inclusion Bodies

The culture broth obtained by the method described above was centrifuged to harvest the cells, which were then suspended in 25 mM Tris-HCl buffer containing 10 mM ethylene diamine tetraacetic acid (pH 7.3). The cells were disrupted by passing through a homogenizer (made by APV Gaulin Inc.) and centrifuged again to harvest the precipitate containing the inclusion bodies.

Example 3

Purification (1) Solubilization of *E. coli* Inclusion Bodies

After washing with 1% Triton X-100 three times, the *E. coli* inclusion bodies were centrifuged at 3,000×g for 30 minutes at 4° C., and then the resultant precipitate was solubilized by sonication in 20 mM Tris-HCl buffer, pH 8.3, 8 M urea, 10 mM DTT, and 1 mM EDTA.

(2) Preparation of Monomers

The solubilized solution was centrifuged at 20,000×g for 30 minutes at 4° C. and the resultant supernatant was collected. The obtained supernatant was subjected to SP-Sepharose FF (Pharmacia AB) equilibrated with 20 mM Tris-HCl buffer pH 8.3, 6 M urea, and 1 mM EDTA, and then, after washing with the same solution, it was eluted with the same solution containing 0.5 M NaCl. The protein in the eluate were sulfonated by adding Na$_2$SO$_3$ and Na$_2$S$_4$O$_6$ to read the final concentration respectively at 111 mM and 13 mM and by incubating at 4° C. for 15 hours. The sulfonated solution was gel-filtrated on Sephacryl S-200 HR (Pharmacia AB) equilibrated with 20 mM Tris-HCl buffer, pH 8.3, 6 M urea, 0.2 M NaCl, and 1 mM EDTA to obtain purified sulfonated monomers of the protein of the invention.

(3) Refolding

The solution of the sulfonated monomers was added into a 9 times volume of 50 mM Na-Glycine buffer pH 9.8, 0.2 M NaCl, 16 TnM CHAPS, 5 mM EDTA, 2 mM GSH (reduction type glutathione), and 1 nM GSSG (oxydation type glutathione) with stirring, and then incubated for 24 hours at 4° C. to oxidize and refold the protein of the invention.

(4) Preparation of Homodimers

The refolding solution was diluted with the same volume of purified water and then by adding 6 N NaCl adjusted pH value to approximately 7.4 and placed to isoelectric precipitation. The precipitates collected by centrifugation at 3,000×g for 20 minutes were solubilized in a solution with 30% acetonitrile containing 0.1% TFA. The solution was diluted with the same volume of purified water and loaded on RESOURCE RPC column (Pharmacia AB) of a reverse-phase HPLC preequilibrated with 25% acetonitrile containing 0.05% TFA, and then eluted with a linear gradient of 25-45% acetonitrile containing 0.05% TFA. The eluate was monitored at 280 nm absorbance. The purified homodimer protein fractions were collected and lyophilized by Speed % ac Concentrator (Servant Co.)

(5) Determination of Physicochemical Properties of the Purified Protein of the Invention a) Analysis of N-Terminal Amino Acid Sequence Analysis of the N-terminal amino acid sequence for the purified proteins was performed using an amino acid sequencer Model 476A (Applied Biosystems Inc.) to confirm the amino acid sequence from the N-terminal to the 30th amino acid as shown in SEQ ID No.:1 of the Sequence Listing.

b) Analysis or Amino Acid Composition

The analysis of amino acid composition of the purified proteins obtained above was performed by an amino acid sequencer (PICO TAG Systems, Waters). The result was shown in Table 1. The number described in Table 1 indicates the number of amino acid residue per a monomer protein.

TABLE 1

| Amino acid | Practical number | Expected number |
|---|---|---|
| Asx | 11.5 | 12 |
| Glx | 10.9 | 11 |
| Ser | 8.4 | 9 |
| Gly | 4.3 | 4 |
| His | 4.0 | 4 |
| Arg | 7.7 | 7 |
| Thr | 5.4 | 6 |
| Ala | 7.3 | 7 |
| Pro | 10.2 | 10 |
| Tyr | 2.9 | 3 |
| Val | 5.7 | 7 |
| Met | 5.1 | 4 |
| ½Cys | 2.6 | 7 |
| Ile | 4.9 | 6 |
| Leu | 10.0 | 10 |
| Phe | 4.0 | 4 |
| Lys | 5.9 | 6 |
| Typ | — | 2 |
| length of the sequence |  | 119 |

—: undetectable c) Analysis by Electrophoresis

Molecular weight of the purified proteins obtained above was confirmed to be about 28 KDa on SDS-PAGE under non-reducing condition.

From the results shown in the above a), b) and c), it is found that the protein of the invention comprises 119 amino acid residues starting from the N-terminal Pro singly.

Example 4

Determination of Biological Activities (1) Activity in Ectopic Bone Formation in Mice.

About 500 μg of the homodimer protein obtained in Example 3 was dissolved and diluted in 50 μl of 10 mM hydrochloric acid, and 1 μg/10 μl, 10 μg/10 μl, and 100 μg/10 μl concentrations of the solution were prepared. Ten μl of each solution was mixed with 150 μl porcine tendon type-I collagen solution (Koken, 0.5%, pH 3, I-AC), neutralized, lyophilized, and the resultant mixture was implanted into pockets created in the thigh muscles of 8-week-old male ICR mice. At day 21 from implantation, the animals were sacrificed and the thighs were excised. After peeling skins off, the incidence of calcified tissues was evaluated by soft X-ray radiography. As shown in Table 2, the implantation of 1 μg/site or more of the dimer protein induced calcified tissue in part of the group of the mice, and 10 and more doses induced calcified tissue in all mice used.

TABLE 2

| Dose of the homodimer protein | Incidence of calcified tissue |
|---|---|
| Control (Type-I collagen alone) | 0/4 |
| 1 μg/site | 3/4 |
| 10 μg/site | 4/4 |
| 100 μg/site | 4/4 |

Figure 2:
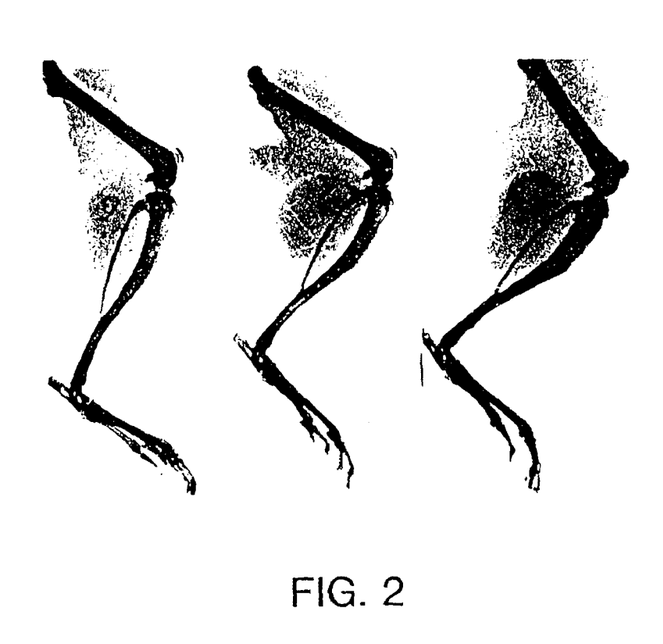
FIG. 2 shows a soft Xray radiograph of the calcified tissue induced in mouse thigh in Example 4 step (1).

FIG. 2 shows typical examples of soft X-ray radiographs of calcified tissue induced by different doses of MP52 protein. FIGS. 2A, 2B and 2C show examples of soft X-ray radiographs of 1 μg the homodimer protein/site-, 10 μg/site- and 100 μg/site-implanted mice thighs, respectively. These radiographs indicate that the homodimer protein induced calcified tissue in the mouse thigh and increased it in a dose-dependent manner. In order to verify if the formed calcified tissues were cartilage or bone, the sections of the fixed mouse thighs into which 10 μg/site the homodimer protein was implanted were stained with von Kossa, Alcian blue or Hematoxylin-eosin.

Figure 3A:
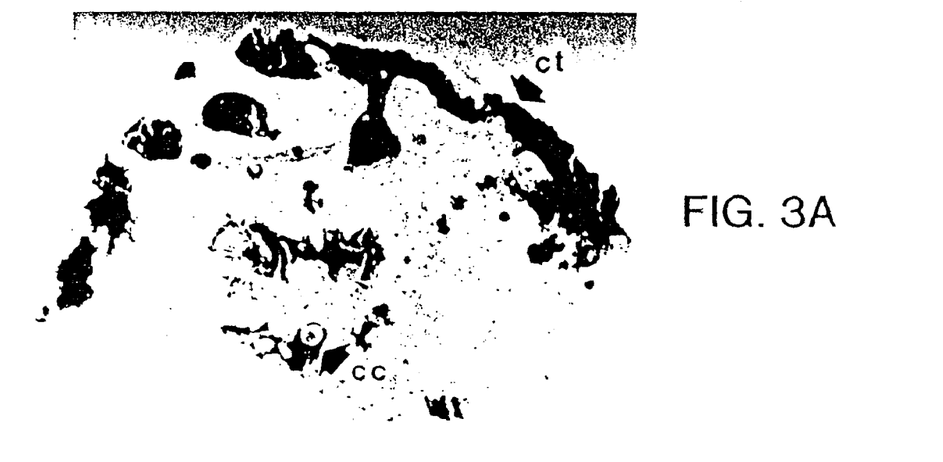
FIG. 3A-3C show light-microscopic photographs of the calcified tissue stained in mouse thigh in Example 4 step (1). The sections are stained with the respective staining methods.
Figure 3B:
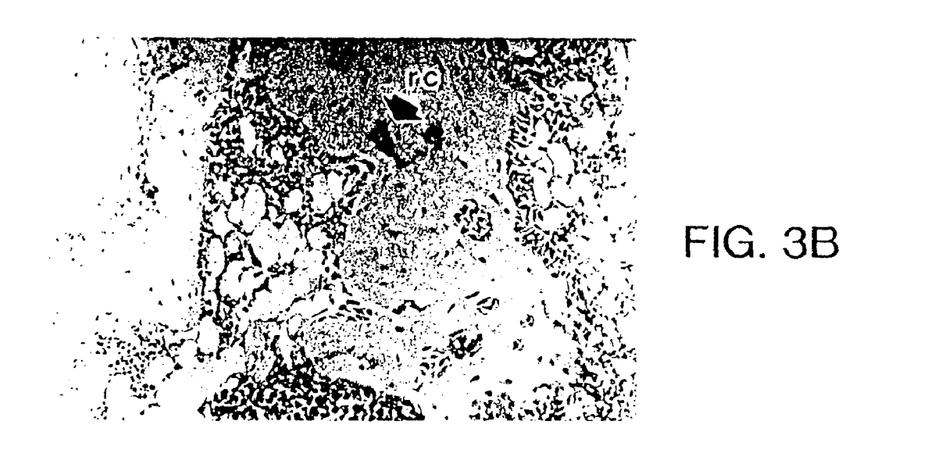
Figure 3C:
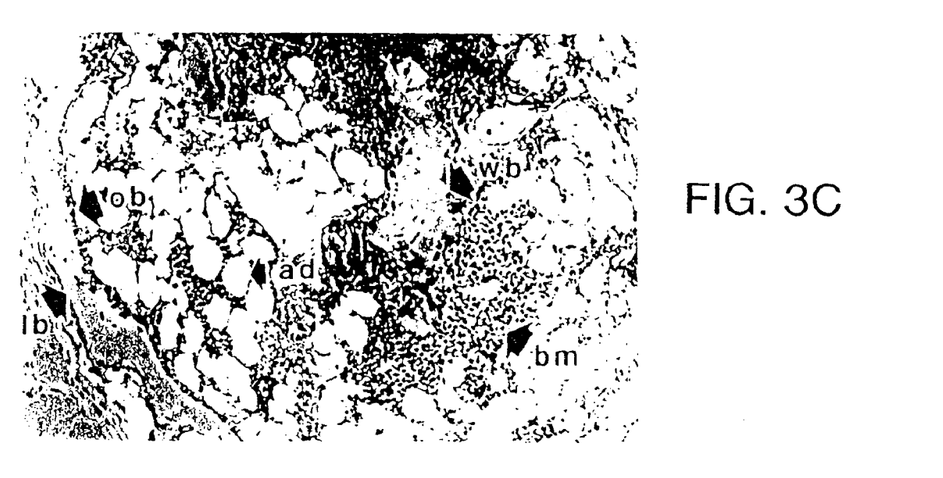
Figure 4A:
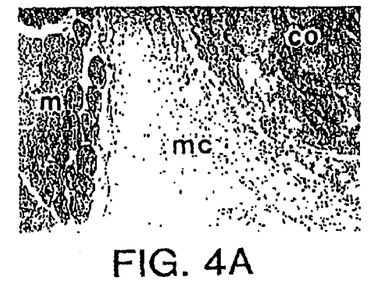
Figure 4B:
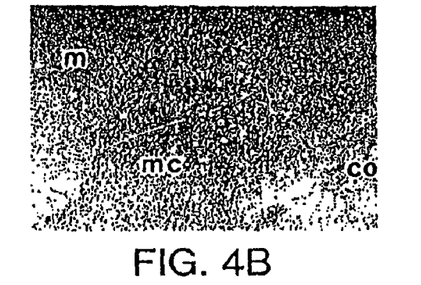
Figure 4C:
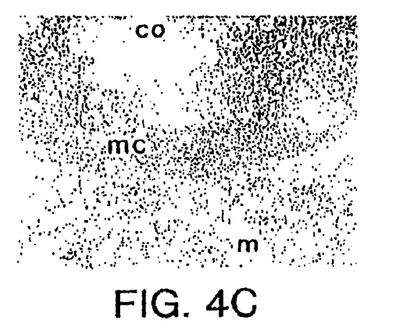
Figure 4D:
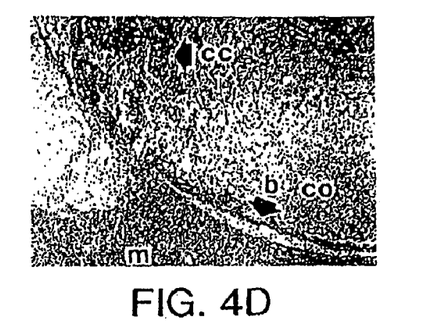
Figure 4E:
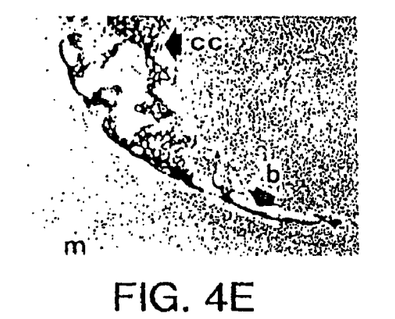
Figure 4F:
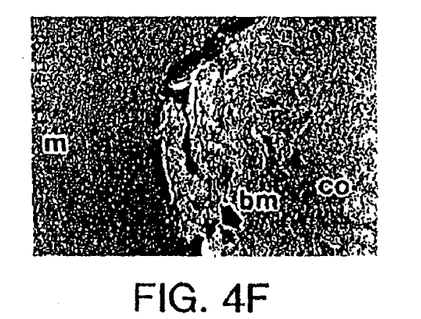
Figure 4G:
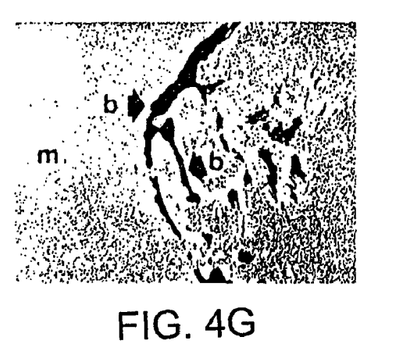
Figure 4H:
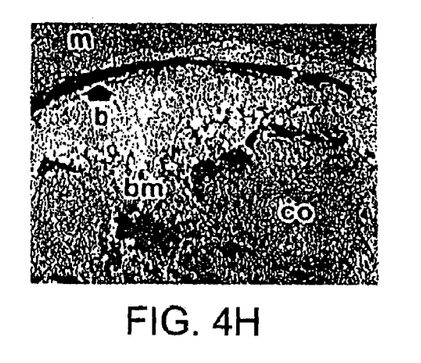

FIG. 3 shows light-microscopic photographs of the sections stained with the respective staining methods. In FIG. 3A (von Kossa staining), areas indicated by ct and cc show calcified tissue and calcified chondrocytes, respectively. In FIG. 3B (Alcian blue staining), an area indicated by rc shows remaining cartilage tissue. In FIG. 3C (Hematoxylin-eosin staining), elements indicated by ad, bm, lb, ob and wb are an adipocyte, bone marrow cells, lamellae bone, osteoblasts, and woven bone, respectively. Thus, it is evident that the implantation of the homodimer protein with Type-I collagen into mouse thighs induces calcified chondrocytes, osteoblasts, and bone marrow cells at the sites.

Thus, the homodimer protein was demonstrated to possess activity in ectopic cartilage and bone formation.

(2) Analysis of Time-Course of Ectopic Bone Formation in Mice

The dimer protein (3 μg) obtained in Example 3 was mixed with Type-I collagen solution and neutralized as described in Example 4 (1), and the lyophilized materials were implanted into the male ICR mouse thighs. At days 3, 7, 10, 14, 21, and 28 from implantation, the thighs were excised and fixed in 10% formalin, and then, sections were stained with Hematoxylineosin or von Kossa. FIG. 4 shows the light-microscopic photographs of the sections stained.

At day 3 (FIG. 4A, Hematoxylin-eosin staining), undifferentiated mesenchymal cells (mc) including morphologically fibrous connective cells appeared in the space between collagen fibers (co) implanted and muscle cells (m). At between days 7 and 10 (FIGS. 4B and 4C, respectively, Hematoxylin-eosin staining), the space was filled with undifferentiated mesenchymal cells (mc) and these cells were hypertrophied and differentiated into precartilagenous tissue. At day 14 (FIG. 4D, Hematoxylin-eosin staining and FIG. 4E, von Kossa staining), calcified cartilage tissue (cc) and bone tissue (b) were observed. At day 21 (FIG. 4D, Hematoxylin-eosin staining and FIG. 4E, von Kossa staining), calcified cartilage tissue was not observed at all, and the tissue observed at day 14 appeared to be replaced into bone (b) with bone marrow (bm). At day 28 (FIG. 4H, Hematoxylineosin staining), there were a large mount of bone marrow cells and formed bone appeared to be under a resorptive process.

Thus, it is evident that the homodimer protein induces endochondral ossification through cartilage formation at ectopic sites, as reported by using other BMPs.

(3) Effect on the Intramembranous Ossification

Figure 5A:
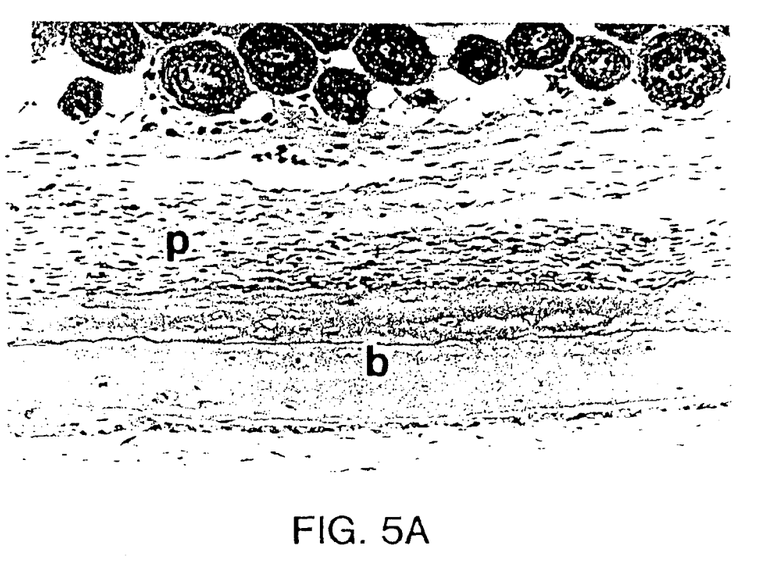
FIG. 5A-5B shows a light-microscopic photograph of rat parietal bone stained in Example 4 step (3). A typical example of microscopic photographs of the section at a homodimer protein 0.1 µg/site-injected site is shown in FIG. 5B in comparison with that of the counter-side of vehicle-injected site (FIG. 5A). The injection of the homodimer protein induced the activation and proliferation of periosteal cells (p), and activated osteoblasts (ob) were observed in and on the parietal bone (b).
Figure 5B:
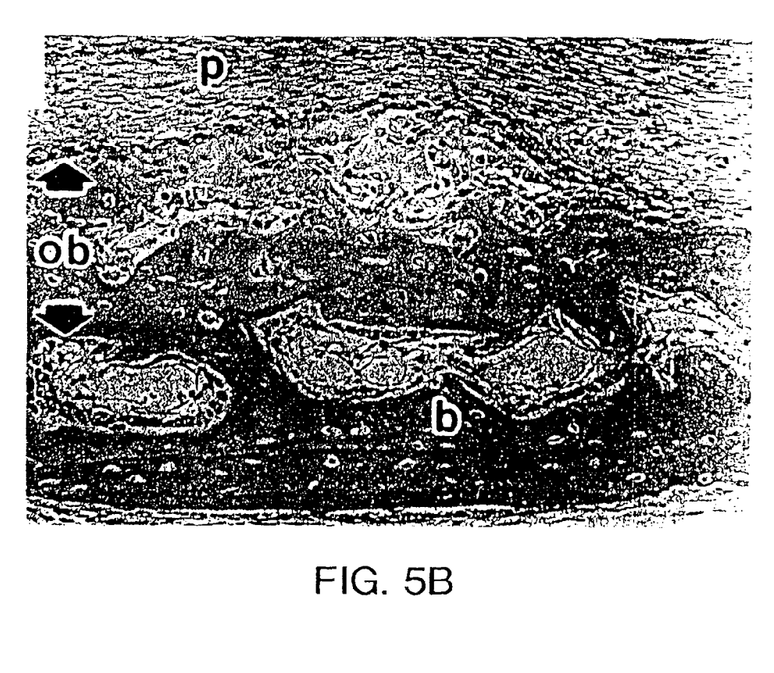

The homodimer protein obtained in Example 3 was dissolved in phosphate-buffered saline (pH 3.4) containing 0.01% human serum albumin, and 0.01 μg/20 μl-, 0.1 μg/20 μl-, and 1 μg/20 μl-concentrations of solutions were prepared. Twenty μl-portion of each solution was injected 12 times once a day onto the periosteum of neonatal rat parietal bone by using a microsyringe from day 1 after birth. The same volume of the vehicle was injected onto the counter-side of parietal bone of each rat. The same volume of the vehicle was also injected onto both sides of parietal bones of control rats. At day 1 from the final injection, the rats were sacrificed and the both sides of parietal bones were excised and fixed, and then, the decalcified sections stained with Hematoxylin-eosin were prepared to measure the thickness of the parietal bones at the injected sites on microscopic photographs. The ratio of the homodimer protein-injected site/vehicle-injected site in the parietal bone thickness of each rat was calculated. As shown in Table 3, the homodimer protein increased parietal bone thickness in a dose-dependent manner. A typical example of microscopic photographs of the section at a homodimer protein 0.1 μg/site-injected site is shown in FIG. 5B in comparison with that of the counter-side of vehicle-injected site (FIG. 5A). The injection of the homodimer protein induced the activation and proliferation of periosteal cells (p), and activated osteoblasts (ob) were observed in and on the parietal bone (b). These results indicate that the homodimer protein stimulated intramembranous ossification when locally injected, and that the homodimer protein is beneficial to the therapies of osteoporosis, bone fracture, and alveolar ridge and periodontal defects.

TABLE 3

| Dose of homodimer protein | Parietal bone thickness (μm) | | |
|---|---|---|---|
| protein (μg/site/day) | Vehicle-injected site (A) | MP52-injected site (B) | Ratio (B/A) |
| 0 (vehicle) | 128 ± 7 | 141 ± 20 | 1.10 ± 0.16 |
| 0.01 | 134 ± 9 | 167 ± 30 | 1.27 ± 0.33 |
| 0.1 | 119 ± 19 | 190 ± 29 | 1.60 ± 0.10* |
| 1 | 132 ± 9 | 225 ± 25 | 1.70 ± 0.14** |

Values represent means ± SD (n = 4),
*p < 0.05,
**p < 0.01 vs. ratio of the group in which vehicle was injected into both the sites (Williams' test).

(4) Effect on the Regeneration of Articular Cartilage

Figure 6A:
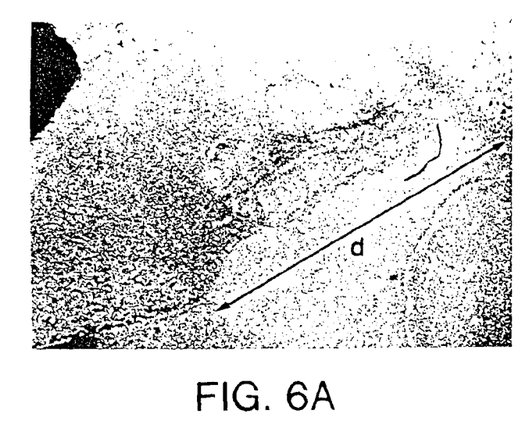
FIG. 6A-6D shows a lightmicroscopic photograph of articular cartilage defects stained in the rabbit femoral head in Example 4 step (4). The dimer protein treated defects (FIGS. 6C and 6D) demonstrated the regeneration of chondrocytes (ch) with extracellular matrices which were stained intensively with Alcian blue, as compared to the Type-I collagen sponge implanted control defects (FIGS. 6A and 6B) which were filled with fibrous tissue (f).
Figure 6B:
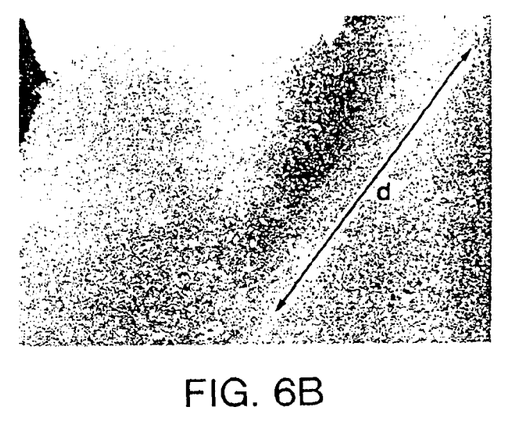
Figure 6C:
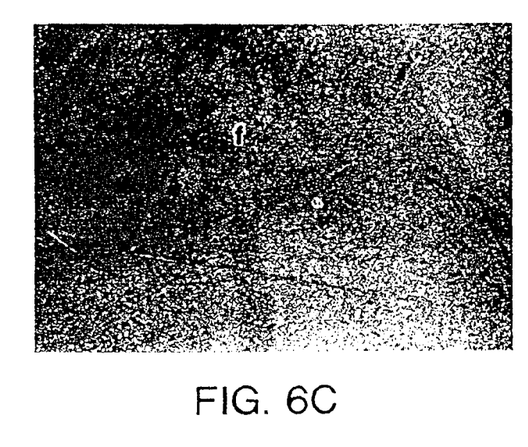
Figure 6D:
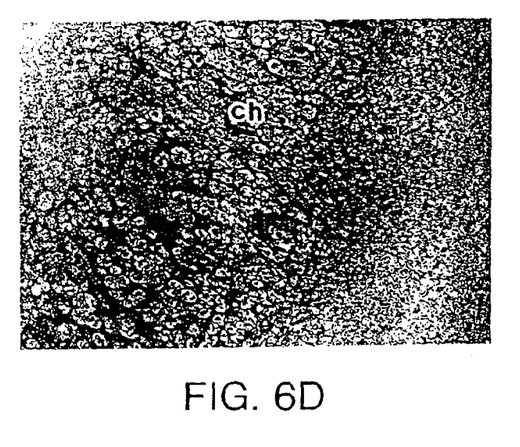
Figure 7A:
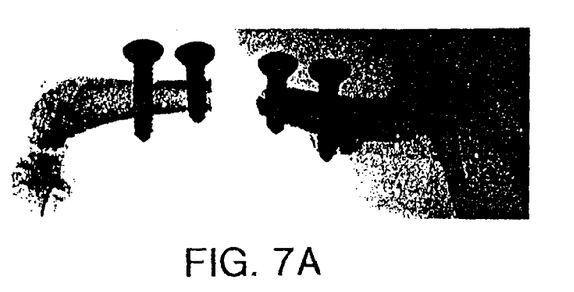
FIG. 7A-7D shows a soft X-ray radiograph of the bone formation in the bone defects of the rat femurs in Example 4 step (5).
Figure 7B:
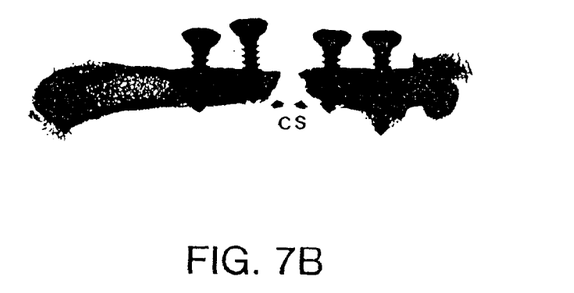
Figure 7C:
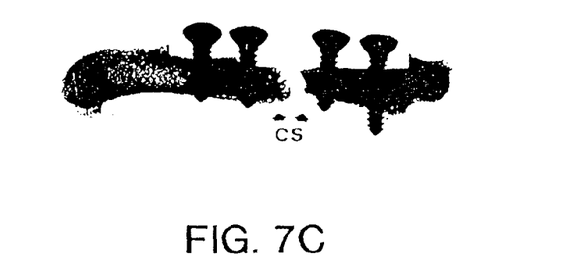
Figure 7D:
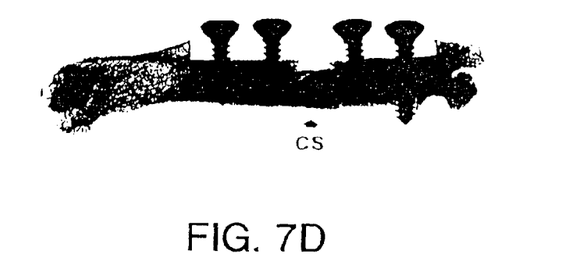

Six 12-week-old male New Zealand White rabbits were used for this study. Right knee skin and articular capsule were cut and a 5×5 mm full thickness osteochondral defect was created in the patellar groove using a dental burr so as not to damage surrounding tendons. The defects were filled with either lyophilized Type-I collagen sponge or with lyophilized Type-I collagen sponge containing 10 μg homodimer protein, prepared as described in Example 4 (1), and then, the cut articular capsule and skin were sutured. Three weeks postoperatively, the rabbits were sacrificed and the femoral heads were excised and fixed in 10% formalin, and then, decalcified sections were stained with Alcian blue. Typical examples of microscopic photographs of the sections were shown in FIG. 6. The dimer protein treated defects (FIGS. 6C and 6D) demonstrated the regeneration of chondrocytes (ch) with extracellular matrices which were stained intensively with Alcian blue, as compared to the Type-I collagen sponge implanted control defects (FIGS. 6A and 6B) which were filled with fibrous tissue (f). The cartilage tissue induced by the dimer protein showed zonal structure including resting chondrocytes, growing chondrocytes and hypertrophied chondrocytes, like that of normal articular cartilage. The chondroinduction by the MP52 protein were observed in the defects of all rabbits used (n=3). These results indicate that the dimer protein is effective to the repair of damaged cartilage tissue in patients such as osteoarthritis.

(5) Effect on the Healing of Bone Fracture and Defects

Thirty male Sprague-Dawley rats (about 15-week-old) were used for this study. Using a lateral approach to the femur, all muscle and periosteal tissue were stripped from the diaphysis. A 5 mm-segmental bone defect was created in the middle region of the right femur shaft with use of dental burr, and then, a special-made polyethylene plate was fixed with stainless screws along the cortex of the femur. Type-I collagen sponges containing 0, 1, 10, and 100 μg of the homodimer protein were prepared as described in Example 4 (1), and implanted into the segmental bone defects and then, the wound was sutured. Just after operation and 12 weeks postoperatively, the defects were evaluated by soft X-ray radiography. As shown in FIGS. 7, 10 and 100 μg/site of the homodimer protein stimulated callus (cs) formation in the defects and formed bony unions, but the effect at 1 μg/site was not clear as compared to the control collagen implanted defect in which only marginal endosteal bone formation was observed. Twelve weeks post-operatively, rats were sacrificed, and the femur with a defect was excised and bone mineral content (accumulated one of mid-three scannings in the defect) was measured by dual energy X-ray absorptiometry (Aloka, Model DCS-600) in a mode with 1 mm scanning width after removing the polyethylene plate. Both ends of the femur with the resin were fixed, then, maximum torsional strength to break the union of specimens were measured by bone strainer system (Malto, model MZ-500D) in a routing speed with 180°/min (Table 4). It shows that the homodimer protein increases both bone mineral content and bone strength at the rat femur defect in which the protein is implanted, and indicates the efficacy of the present protein for fracture healing and bone reconstruction of the defect.

TABLE 4

| Dose of homodimer protein (μg/site) | Bone Mineral Content in rat femur defect (mg) | Maximum Torsional Strength (Kgf · cm) | Number |
|---|---|---|---|
| collagen alone | 120.2 ± 24.5 | 2.92 ± 0.09 | 6 |
| 1 | 176.9 ± 36.4 | 6.24 ± 1.00 | 8 |
| 10 | 277.4 ± 63.9 | 9.35 ± 3.14 | 8 |
| 100 | 374.8 ± 67.1* | 40.34 ± 7.64* | 8 |

Values represent means ± SE,
*p < 0.05 vs. collagen alone group (Student's t-test).

From the results in Example 4, the homodimer protein of the invention was found to have a cartilage and bone morphogenetic activity.

The protein composed of a homodimer of the protein having an amino acid sequence in SEQ ID No.:1 of the Sequence Listing has a cartilage and bone morphogenetic activity and is useful as a pharmaceutical composition for treating cartilage and bone diseases. Furthermore, the protein of the invention can be prepared on an industrial scale and in a pure form by a gene engineering process culturing *E. coli* transformed with a higher copy number expression vector for said protein.

BRIEF EXPLANATION OF DRAWINGS

In FIG. 3A (von Kossa staining), areas indicated by ct and cc show calcified tissue and calcified chondrocytes, respectively. In FIG. 3B (Alcian blue staining), an area indicated by rc shows remaining cartilage tissue. In FIG. 3C (Hematoxylin-eosin staining), elements indicated by ad, bm, lb, ob and wb are an adipocyte, bone marrow cells, lamellae bone, osteoblasts, and woven bone, respectively. Thus, it is evident that the implantation of the homodimer protein with Type-I collagen into mouse thighs induces calcified chondrocytes, osteoblasts, and bone marrow cells at the sites.

FIG. 4A-4H shows a light-microscopic photograph of the time-coursed calcified tissue stained in mouse thigh in Example 4 step (2). At day 3 (FIG. 4A, Hematoxylin-eosin staining), undifferentiated mesenchymal cells (mc) including morphologically fibrous connective cells appeared in the space between collagen fibers (co) implanted and muscle cells (m). At between days 7 and 10 (FIGS. 4B and 4C, respectively, Hematoxylin-eosin staining), the space was filled with undifferentiated mesenchymal cells (mc) and these cells were hypertrophied and differentiated into precartilagenous tissue. At day 14 (FIG. 4D, Hematoxylin-eosin staining and FIG. 4E, von Kossa staining), calcified cartilage tissue (cc) and bone tissue (b) were observed. At day 21 (FIG. 4D, Hematoxylin-eosin staining and FIG. 4E, von Kossa staining), calcified cartilage tissue was not observed at all, and the tissue observed at day 14 appeared to be replaced into bone (b) with bone marrow (bm). At day 28 (FIG. 4H, Hematoxylineosin staining), there were a large amount of bone marrow cells and formed bone appeared to be under a resorptive process.

As shown in FIGS. 7A-7D, 10 and 100 µg/site of the homodimer protein stimulated callus (cs) formation in the defects and formed bony unions, but the effect at 1 µg/site was not clear as compared to the control collagen implanted defect in which only marginal endosteal bone formation was observed.

The invention claimed is:

1. A process for preparing an isolated protein comprising the amino acid sequence shown in SEQ ID NO: 1, comprising culturing E. coli transformed with a plasmid comprising a DNA sequence encoding SEQ ID NO: 1, under conditions suitable for expressing said protein wherein said protein has cartilage and/or bone morphogenetic activity, wherein proteins according to SEQ ID NO: 1 with either a) an Ala or b) a Met-Ala at the N-terminus are not expressed and are not present in said isolated protein, and wherein the plasmid comprises a DNA encoding the amino acid sequence shown in SEQ ID NO: 1 with a methionine at the N-terminus of SEQ ID NO: 1.

2. A process for preparing a homodimer protein comprising the amino acid sequence shown in SEQ ID NO: 1, comprising constructing a plasmid comprising DNA encoding the amino acid sequence shown in SEQ ID NO: 1 with a methionine at the N-terminus of SEQ ID NO: 1, introducing the plasmid into E. coli by transformation, culturing said E. coli, solubilizing any inclusion bodies obtained by culturing said E. coli, purifying monomer protein from the solubilized inclusion bodies, refolding the monomer protein into a dimer protein and purifying the dimer protein.

3. A plasmid comprising a DNA encoding a polypeptide, wherein said polypeptide consists of the amino acid sequence shown in SEQ ID NO: 1 with an additional methionine at the N-terminus of SEQ ID NO: 1, and wherein said polypeptide (a) can be expressed free of proteins according to SEQ ID NO: 1 which have an Ala or Met and Ala at the N-terminus,
(b) can be expressed in E. coli, and
(c) has cartilage and/or bone morphogenetic activity.

4. A process for the preparation of an isolated protein consisting of the 119 amino acids as shown in SEQ ID NO: 1, wherein said protein is free of proteins of SEQ ID NO: 1 with an Ala or a Met-Ala at the N-terminus and wherein said protein has cartilage and/or bone morphogenetic activity, comprising (a) constructing a plasmid encoding a protein consisting of the 119 amino acids as shown in SEQ ID NO: 1 with a methionine at the N-terminus of SEQ ID NO: 1, introducing the plasmid into E. coli by transformation, culturing the E. coli to obtain inclusion bodies, solubilizing the inclusion bodies, purifying the protein from the solubilized inclusion bodies, refolding the protein into a homodimer protein and purifying the homodimer protein.

5. The process according to claim 4, wherein the plasmid comprises the sequence of SEQ ID NO: 4 with an ATG start codon at the 5' terminus of SEQ ID NO: 4.

6. The process according to claim 5, further comprising substituting the 5' terminus of the nucleotide sequence of SEQ ID NO: 4 from position 1 to position 21 by the DNA sequence consisting of residues 7-27 of SEQ ID NO: 2 (CCA CTA GCA ACT CGT CAG GGC).

* * * * *